United States Patent [19]

Fukumoto et al.

[11] Patent Number: 4,696,184

[45] Date of Patent: Sep. 29, 1987

[54] DEVICE FOR MEASURING THE ABSOLUTE VALUE OF THE DENSITY OF SALTS IN ATMOSPHERE

[75] Inventors: Takaaki Fukumoto, Kishiwada; Toshiaki Ohmori, Amagasaki, both of Japan

[73] Assignee: Mitsubishi Denki Kabushiki Kaisha, Tokyo, Japan

[21] Appl. No.: 790,932

[22] Filed: Oct. 24, 1985

[30] Foreign Application Priority Data

Dec. 20, 1984 [JP] Japan .................... 59-270269

[51] Int. Cl.$^4$ ............................ G01N 27/00
[52] U.S. Cl. .................... 73/32 R; 324/439; 204/400; 204/409
[58] Field of Search ............... 73/32 R, 19, 23, 28; 204/1 A, 409, 400; 324/439, 450, 65 R; 422/88, 90

[56] References Cited

U.S. PATENT DOCUMENTS

| | | | |
|---|---|---|---|
| 2,758,079 | 8/1956 | Eckfeldt | 324/439 |
| 3,267,361 | 8/1966 | Maddox | 324/439 |
| 3,493,857 | 2/1970 | Silverman | 324/65 R |
| 3,751,967 | 8/1973 | Fick et al. | 73/23 |
| 3,942,792 | 3/1976 | Topol | 73/19 |
| 4,083,766 | 4/1978 | Landon et al. | 324/439 |
| 4,569,224 | 2/1986 | Fukumoto et al. | 73/32 R |

*Primary Examiner*—Stewart J. Levy
*Assistant Examiner*—Hezron E. Williams
*Attorney, Agent, or Firm*—Birch, Stewart, Kolasch & Birch

[57] ABSTRACT

A device for measuring the absolute value of the density of salts in an atmosphere, which comprises an airtight water tank containing super pure water; a means for supplying super pure water to the airtight water tank; a means for bubbling a predetermined quantity of air in the atmosphere into the super pure water being provided in the airtight water tank; a means for exhausting the super pure water in the airtight water tank after the bubbling; a sodium ion analyzer for measuring the density of sodium ions in the exhausted super pure water; and a means for introducing the outside air to the bubbling means in accordance with the pressure difference between the inside and the outside of the water tank.

16 Claims, 3 Drawing Figures

F I G .1.
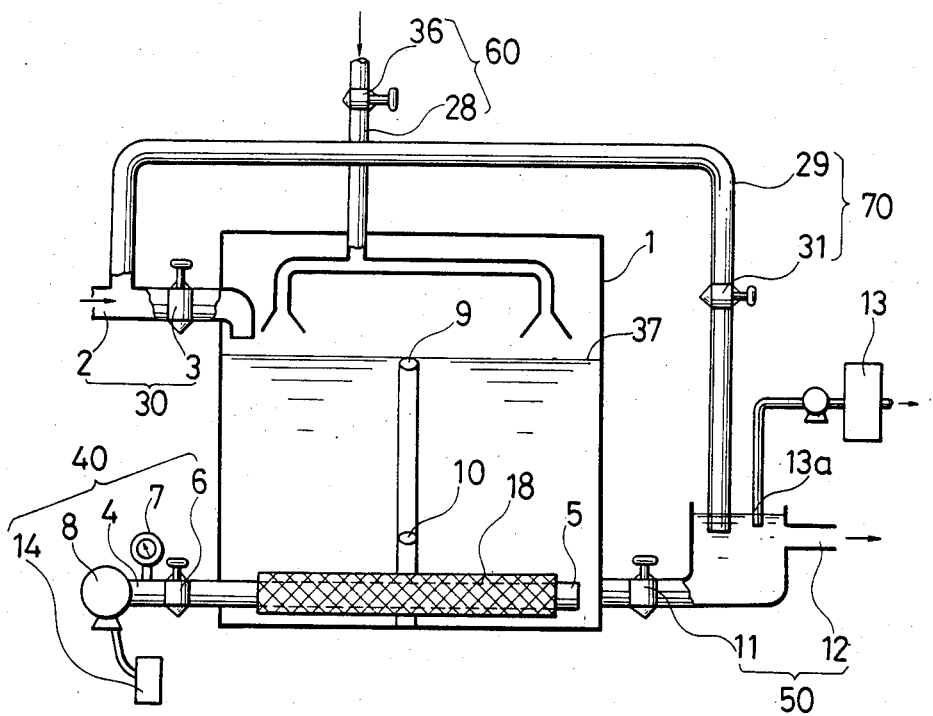
F I G .2.
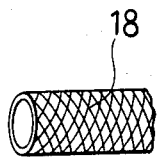

DEVICE FOR MEASURING THE ABSOLUTE VALUE OF THE DENSITY OF SALTS IN ATMOSPHERE

FIELD OF THE INVENTION

The present invention relates to a device for measuring the absolute value of the density of salts in an atmosphere and continuously monitoring the same.

BACKGROUND OF THE INVENTION

FIGS. 1 and 2 show a device for measuring the absolute value of the density of salts in an atmosphere already invented by the inventor. In the FIGS., the reference numeral 1 designates an airtight water tank of a predetermined capacity which contains the super pure water 37 of a predetermined quantity, the resistivity of which is above 15MΩ.cm. The tank 1 is made up of a material from which any dissolved material including sodium ions does not soak out, such as a transparent vinyl chloride. The numeral 2 designates a pipe for supplying the super pure water to the tank 1. The numeral 3 designates a valve provided at the pipe 2. The pipe 2 and the valve 3 constitute a means 30 for supplying the water. The numeral 5 designates a bubbling pipe for bubbling air in the atmosphere into the super pure water 37 in the tank 1 to dissolve the salts in the atmosphere into the super pure water 37. The numerals 4, 6, 8, 7, and 14 designate a pipe, a valve, a pump, a flow meter, and a timer, all of which constitute a means 40 for supplying air in the atmosphere to the bubbling pipe 5. The numerals 9 and 10 designate flow switches to hold the level of the super pure water 37 contained in the tank 1 at predetermined levels. The numeral 12 designates an exhaust pipe for exhausting the super pure water 37 contained in the tank 1 to the outside. The numeral 11 designates a valve provided at the exhaust pipe 12. The exhaust pipe 12 and the valve 11 together constitute a means 50 for exhausting the water. The numeral 13 designates a sodium ion analyzer for measuring the density of Na+ ions in the exhausted super pure water of a predetermined quantity. The material taking inlet or measuring tank 13a of the analyzer 13 is placed in the exhausted water.

The numeral 29 designates a bypass pipe for supplying super pure water at the water supplying means 30 to the material taking inlet 13a of the sodium ion analyzer 13 while bubbling through bypass. This bypass pipe 29 is located upstream of the water flow from the water tank 1 to the exhaust pipe 12 relative to the material taking inlet 13a. The numeral 31 designates a valve provided at the pipe 29. The pipe 29 and the valve 31 constitute a bypass means 70 for supplying super pure water through a bypass, and the bypass means 70 and the sodium ion analyzer 13 constitute a background value measuring means for measuring the density of sodium ions in the super pure water at the water supplying means 30 while bubbling occurs. The numeral 28 designates a pipe for supplying super pure water for backwashing the water tank 1, and the numeral 36 designates a valve provided at the pipe 28. The pipe 28 and the valve 36 constitute a means 60 for washing the water tank 1. The reference numeral 18 designates a mesh provided covering the outer surface of the cylindrical bubbling pipe 5. This mesh 18 can be provided inside the bubbling pipe 5.

The device will be operated as follows:

First, the valve 3 in the means 30 for supplying the water is opened, and the super pure water 37, the resistivity of which is above 15MΩ.cm, is supplied to the airtight water tank 1 through the pipe 2. When the flow switch 9 operates, the valve 3 in the water supplying means 30 is closed to stop the supply of the super pure water 37 to the tank 1. Thus, the airtight water tank 1 is filled up with the super pure water 37 of a predetermined quantity. When the valve 6 in the means 40 for supplying air in the atmosphere is opened and the pump 8 is operated, air in the atmosphere is sent to the bubbling pipe 5 through the pipe 4 at a constant flow rate for a predetermined time. The bubbling pipe 5 operates to bubble the air into the super pure water 37 in the tank 1 to make the salts, that is, NaCl in the air dissolved into the super pure water 37. When the bubbling is concluded, the valve 6 is closed, the valve 11 in the means 50 for exhausting the water is opened, and the super pure water in the tank 1 is exhausted to the outside through the pipe 12 at a constant flow rate caused by its positional potential. The sodium ion analyzer 13 with its material taking inlet 13a sunk placed in the exhausted super pure water operates to measure the density of Na+ ions in the super pure water. Then, the absolute value of the density of salts in the atmosphere is obtained from the density of Na+ ions in the super pure water measured by the sodium ion analyzer 13 by executing an operation including the mass-conversion between Na+ and NaCl.

Caused by the exhaustion of the super pure water, the flow switch 10 operates to open the valve 3, and thereafter, the above mentioned measuring operation is repeated. This enables continuous monitoring. In this case, the quantity of the air to be supplied is measured by the flow meter 7 and is regulated by the valve 6. The time period during when the air is supplied can be regulated by the timer 14. Furthermore, the time period during when the super pure water is supplied can be regulated by a means (not shown) provided in the water supplying means 30.

In the bubbling operation, the super pure water is supplied from the water supplying means 30 to the material taking inlet 13a of the sodium ion analyzer 13 at a predetermined flow rate by a bypass means 70 for supplying super pure water through a bypass, whereby the background value of the sodium ions, that is, the density of sodium ions in the super pure water before bubbling is measured by the sodium ion analyzer 5. After the super pure water to which air has been bubbled is exhausted, super pure water is supplied to the water tank 1 from above the tank 1 by the pipe 28 which is branched into two pipes inside the water tank 1, and the water tank 1 is washed thereby. By repeating the above-described operation, it is possible to measure and continuously monitor the absolute value of the salts in the atmosphere with a stable background value of sodium ions, resulting in a highly reliable measurement.

According to this device, a bypass means for supplying the super pure water to the sodium ion analyzer through a bypass is provided so as to stabilize the background value of the sodium ion analyzer, and a means for washing the water tank using the super pure water is provided so as to remove the remaining sodium ions in the tank. Such construction can provide a highly reliable result.

Furthermore, bubbles generated from the bubbling pipe 5 are minimized by the mesh 18, and therefore, the surface area ratio of the air and the super pure water contacting it is large. Furthermore, the velocity of the air supplied to the bubbling pipe 5 is controlled by the valve 6 and the flow meter 7 to be equal to that of the air flow outside the device. For example, when the device is installed outside, the above-mentioned velocity is made equal to the velocity of the outside air flow, and when the device is installed in a clean room which is ventilated, the velocity is made equal to the velocity of the air flow inside the room. This makes it possible to obtain a stable result regardless of changes of the state of the atmosphere, and it is especially effective for use in a region near the sea.

Furthermore, it is, of course, possible to control the quantity of air and the time period for bubbling depending on the density of salts in the atmosphere where the measurement is conducted. The sodium ion analyzer has a measuring range from 0.1 ppb to 1,000 ppb, and it may be provided with a function to output an alarm signal when the measured result exceeds the upper limit of the measuring range as a countermeasure against a high density of salts in a seaside region.

In this device, however, there is a disadvantage that the water in the tank 1 is contaminated by the oil mist of the pump 8 because air is supplied to the tank 1 from the outside by the pump 8. Furthermore, it is difficult to conduct a continuous monitoring because the valves are all manually operated.

SUMMARY OF THE INVENTION

The present invention is directed to solve the problems pointed out above, and has for its object to provide a device for measuring the absolute value of the density of salts in the atmosphere and continuously monitoring the same so as to be capable of eliminating contaminations by a pump.

Another object of the present invention is to provide a device for measuring the absolute value of the density of salts in the atmosphere which is capable of conducting automatic continuous monitoring easily.

Other objects and advantages of the present invention will become apparent from the detailed description given hereinafter; it should be understood, however, that the detailed description and specific embodiment are given by way of illustration only, since various changes and modifications within the spirit and scope of the invention will become apparent to those skilled in the art from this detailed description.

According to the present invention, there is provided a device for measuring the absolute value of the density of salts in atmosphere, which comprises: an airtight water tank containing super pure water; a means for supplying super pure water to the airtight water tank; a means for bubbling a predetermined quantity of air in an atmosphere into the super pure water of a predetermined quantity, the means provided in the airtight water tank; a means for exhausting the super pure water in the airtight water tank after the bubbling; a sodium ion analyzer for measuring the density of sodium ions in the exhausted super pure water; and a means for introducing the outside air to the bubbling means in accordance with the pressure difference between the inside and the outside of the water tank.

BRIEF DESCRIPTION OF THE DRAWINGS

FIG. 1 is a schematic diagram showing a device for measuring the absolute value of the density of salts in an atmosphere already invented by the inventors FIG. 2 is a perspective view of the mesh 18 in FIG. 1.

DETAILED DESCRIPTION OF THE PREFERRED EMBODIMENTS

Figure 3:
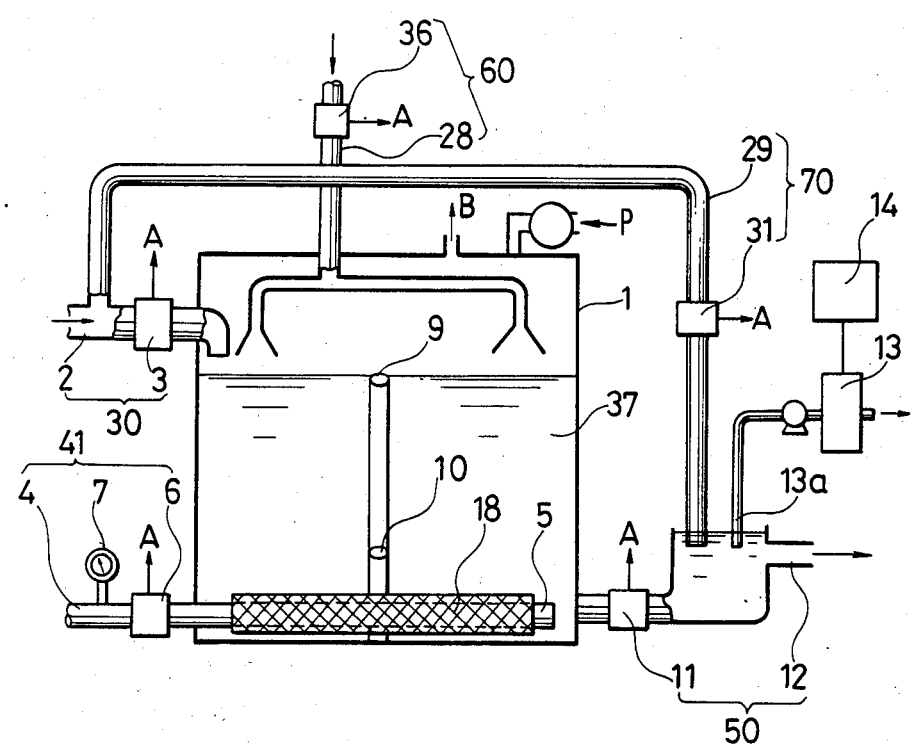
FIG. 3 is a schematic diagram showing a device for measuring the absolute value of the density of salts in an atmosphere as an embodiment of the present invention.

Reference will now be particularly made to FIG. 3 which shows an embodiment of the present invention.

In the Figure, the same reference numerals are used to designate the same or corresponding elements as those in FIG. 1.

In this embodiment there is provided a pressure reduction system B for reducing the air pressure in the airtight water tank 1 at the upper wall of the water tank 1, and this system B supplies air in the atmosphere to the bubbling pipe 5 in accordance with the difference between the pressure in the tank 1 and that on the outside as measured by pressure difference measuring device P, which may, for example, be a manometer. Therefore, the air supplying pipe 4, the valve 6, the flow meter 7, and the pressure reduction system B constitute an air introduction means 41 for introducing air to the bubbling pipe 5 in this embodiment. Furthermore, the valves 3, 11, 6, 31, and 36 in the super pure water supplying means 30, the water exhaust means 50, the air introduction means 41, the super pure water bypass supplying means 70, and the tank washing means 60 are all controlled by a valve control system A so as to conduct an automatic continuous monitoring. The reference numeral 14 designates a recording system connected to the sodium ion analyzer 13 so as to conduct an automatic continuous recording of the measured result.

The main operation for measuring and continuously monitoring the absolute value of the density of salts in the atmosphere is the same as that of the device of FIG. 1. In this embodiment the air is supplied to the bubbling pipe 5, not by the pump 8 as done in the device of FIG. 1, but rather by the pressure reduction system B in accordance with the pressure difference between the pressure in the tank 1 and that on the outside. Accordingly, there arises no contamination of the air and super pure water by the oil mist of the pump. Furthermore, all the valves 3, 11, 6, 31 and 36 are automatically controlled to be opened or closed by electric signals, whereby an automatic continuous monitoring is easily realized.

As evident from the foregoing, according to the present invention, air is introduced to the bubbling pipe in accordance with the pressure difference between the inside and the outside of the water tank by a pressure reduction system provided at the water tank, whereby the influence of contamination caused by the oil mist of a pump is removed. This results in an absolute value of the density of salts in atmosphere with a high accuracy. Furthermore, all the valves in the device are automatically controlled to be opened or closed, thereby enabling one to conduct automatic continuous monitoring easily.

What is claimed is:

1. A measuring device for measuring the absolute value of the density of salts in an atmosphere, which comprises:
   a substantially airtight water tank containing super pure water of a predetermined quantity;

a supplying means operatively associated with said water tank for supplying super pure water to said water tank;

a bubbling means disposed in said water tank for bubbling a predetermined quantity of atmosphere into said super pure water contained in said water tank;

an exhausting means operatively associated with said water tank for exhausting said super pure water from said water tank;

a sodium ion analyzer means operatively associated with said exhaust means for measuring the density of sodium ions in said super pure water after said super pure water is exhausted from said exhaust means; and an introduction means operatively associated with said water tank and said bubbling means for introducing said atmosphere to said bubbling means based upon the pressure differences between the inside of said water tank and said atmosphere.

2. A measuring device as defined in claim 1, which further includes a bypass means operatively associated with said supply means and said sodium ion analyzer means for supplying said super pure water directly from said supplying means to said sodium ion analyzer means so that said sodium ion analyzer means may compare the sodium ion density of said super pure water supplied by said bypass means with that of said super pure water exhausted by said exhaust means.

3. A measuring device as defined in claim 2, which further includes a washing means disposed in said water tank for washing said water tank with said super pure water.

4. A measuring device for measuring the absolute value of the density of salts in an atmosphere, which comprises:

a substantially airtight water tank containing super pure water of a predetermined quantity;

a supplying means operatively associated with said water tank for supplying through a first valve means said super pure water to said water tank;

a bubbling means disposed in said water tank for bubbling a predetermined quantity of air in an atmosphere into the said super pure water contained in said water tank;

an exhausting means operatively associated with said water tank for exhausting through a second valve means said super pure water from said water tank;

a sodium ion analyzer means operatively associated with said exhaust means for measuring the density of sodium ions in said super pure water after said super pure water is exhausted from said exhaust means;

an introduction means operatively associated with said water tank and said bubbling means for introducing through a third valve means said atmosphere to said bubbling means based upon the pressure difference between the inside of said water tank and said atmosphere; and an electrical valve control means for electrically controlling the opening and closing of all said valve means so as to conduct an automatic continuous monitoring of the density of salts in said atmosphere.

5. A measuring device as defined in claim 4, which further includes a bypass means for supplying through a fourth valve means said super pure water directly from said supplying means to sodium ion analyzer means so that said sodium ion analyzer means may compare the sodium ion density of said super pure water supplied by said bypass means with that of said super pure water exhausted by said exhaust means, said fourth valve means being electrically controlled by said electrical valve control means.

6. A measuring device as defined in claim 4, which further includes a washing means disposed in said water tank for washing said water tank with said super pure water supplied through a fifth valve means, said fifth valve means being electrically controlled by said electrical valve control means.

7. A measuring device as defined in claim 2, wherein said bubbling means comprise a bubbling pipe;
said exhausting means comprises an exhaust pipe;
said bypass means comprises a bypass pipe; and
said sodium ion analyzer means comprises a sodium ion analyzer device operatively associated with a measuring tank means which receives said super pure water from said exhaust pipe and from said bypass pipe.

8. A measuring device as defined in claim 5, wherein said bubbling means comprises a bubbling pipe;
said exhausting means comprises an exhaust pipe;
said bypass means comprises a bypass pipe; and
said sodium ion analyzer means comprises a sodium ion analyzer device operatively associated with a measuring means which receives said super pure water from said exhaust pipe and from said bypass pipe.

9. A measuring device as defined in claim 2, further including a recording system means for recording the density of salts in said atmosphere as measured by said sodium ion analyzer.

10. A measuring device as defined in claim 5, further including a recording system means for recording the density of salts in said atmosphere as measured by said sodium ion analyzer.

11. A measuring device as defined in claim 7, wherein said bubbling pipe further includes a mesh means which covers said bubbling pipe, said mesh means increasing the surface area contact between said atmosphere and said super pure water when said bubbling pipe bubbles said atmosphere into said super pure water.

12. A measuring device as defined in claim 8, wherein said bubbling pipe further includes a mesh means which covers said bubbling pipe, said mesh means increasing the surface area contact between said atmosphere and said super pure water when said bubbling pipe bubbles said atmosphere into said super pure water.

13. A method for measuring the absolute value of the density of salts in an atmosphere, which comprises:

supplying super pure water from a supplying means into a substantially airtight water tank;

introducing atmosphere, based upon the pressure difference between the inside of said water tank and said atmosphere, through a bubbling means into said super pure water contained in said water tank so as to dissolve salts contained in said atmosphere into said super pure water;

exhausting said super pure water from said water tank into a sodium ion analyzer means; and measuring the density of said salts in said super pure water with said sodium analyzer means, whereby the salt content in said atmosphere can be determined.

14. A method as defined in claim 13, wherein said atmosphere is air.

15. A method for measuring the absolute value of the density of salts in an atmosphere, which comprises:
   supplying pure water from a supplying means through a first valve means into a substantially airtight water tank;
   introducing atmosphere, based upon the pressure difference between the inside of said water tank and said atmosphere, through a second valve means and then through a bubbling means into said super pure water contained in said water tank so as to dissolve salts contained in said atmosphere into said super pure water;
   exhausting said super pure water through a third valve means from said water tank into a sodium ion analyzer means;
   measuring the density of said salts in said super pure water with said sodium ion analyzer means; and
   electrically controlling all said valve means so as to conduct an automatic continuous monitoring of the density of said salts in said super pure water and said atmosphere.

16. A method as defined in claim 15, wherein said atmosphere is air.

* * * * *